United States Patent
Craig

(10) Patent No.: US 7,294,214 B2
(45) Date of Patent: *Nov. 13, 2007

(54) MEDICAL DEVICES

(75) Inventor: Charles Horace Craig, Lakeside, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 531 days.

This patent is subject to a terminal disclaimer.

(21) Appl. No.: 10/338,223

(22) Filed: Jan. 8, 2003

(65) Prior Publication Data

US 2004/0129347 A1    Jul. 8, 2004

(51) Int. Cl.
*C22C 30/00* (2006.01)

(52) U.S. Cl. .................. 148/442; 148/325; 420/36; 420/583

(58) Field of Classification Search ............. 148/325, 148/442; 420/583, 36, 35, 34
See application file for complete search history.

(56) References Cited

U.S. PATENT DOCUMENTS

| | | | |
|---|---|---|---|
| 3,868,956 A | 3/1975 | Altidi et al. | |
| 4,253,869 A * | 3/1981 | Prosen .................. 420/440 | |
| 4,512,338 A | 4/1985 | Balko et al. | |
| 4,553,545 A | 11/1985 | Maass et al. | |
| 4,580,568 A | 4/1986 | Gianturco | |
| 4,733,665 A | 3/1988 | Palmaz | |
| 4,739,762 A | 4/1988 | Palmaz | |
| 4,762,128 A | 8/1988 | Rosenbluth | |
| 4,776,337 A | 10/1988 | Palmaz | |
| 4,800,882 A | 1/1989 | Gianturco | |
| 4,856,516 A | 8/1989 | Hillstead | |
| 4,886,062 A | 12/1989 | Wiktor | |
| 4,958,625 A | 9/1990 | Bates et al. | |
| 4,969,458 A | 11/1990 | Wiktor | |
| 5,019,337 A * | 5/1991 | Waterstrat .................. 420/580 | |
| 5,090,419 A | 2/1992 | Palestrant | |
| 5,102,417 A | 4/1992 | Palmaz | |
| 5,104,404 A | 4/1992 | Wolff | |
| 5,133,732 A | 7/1992 | Wiktor | |
| 5,192,307 A | 3/1993 | Wall | |
| 5,195,969 A | 3/1993 | Wang et al. | |
| 5,195,984 A | 3/1993 | Schatz | |
| 5,270,086 A | 12/1993 | Hamlin | |
| 4,733,665 A | 1/1994 | Palmaz | |

(Continued)

FOREIGN PATENT DOCUMENTS

WO    WO 01/41829    6/2001

(Continued)

OTHER PUBLICATIONS

ASM International Materials, Park City, Ohio, Metallographer's Guide: Practices and Procedures For Iron and Steels, Chapter 1,"Introduction to Steels and Cast Irons", p. 3, Table 1.1.*

(Continued)

*Primary Examiner*—Scott Kastler
(74) *Attorney, Agent, or Firm*—Fish & Richardson P.C.

(57) ABSTRACT

Alloy compositions suitable for fabricating medical devices, such as stents, are disclosed. In certain embodiments, the compositions have small amounts of nickel, e.g., the compositions can be substantially free of nickel.

59 Claims, 6 Drawing Sheets

U.S. PATENT DOCUMENTS

| | | | |
|---|---|---|---|
| 5,282,823 A | 2/1994 | Schwartz et al. | |
| 5,354,308 A | 10/1994 | Simon et al. | |
| 5,395,390 A | 3/1995 | Simon et al. | |
| 5,395,583 A * | 3/1995 | Potgieter et al. | 420/67 |
| 5,421,955 A | 6/1995 | Lau et al. | |
| 5,443,496 A | 8/1995 | Schwartz et al. | |
| 5,449,373 A | 9/1995 | Pinchasik et al. | |
| 5,514,154 A | 5/1996 | Lau et al. | |
| 5,591,226 A | 1/1997 | Trerotola et al. | |
| 5,674,242 A | 10/1997 | Phan et al. | |
| 5,735,893 A | 4/1998 | Lau et al. | |
| 5,766,238 A | 6/1998 | Lau et al. | |
| 5,780,807 A | 7/1998 | Saunders | |
| 5,902,475 A | 5/1999 | Trozera et al. | |
| 6,056,776 A | 5/2000 | Lau et al. | |
| 6,066,167 A | 5/2000 | Lau et al. | |
| 6,146,404 A | 11/2000 | Kim et al. | |
| 4,776,337 A | 12/2000 | Palmaz | |
| 6,171,327 B1 | 1/2001 | Daniel et al. | |
| 6,267,921 B1 | 7/2001 | Montagnon et al. | |
| 6,325,766 B1 | 12/2001 | Anderson et al. | |
| 6,325,824 B2 * | 12/2001 | Limon | 623/1.2 |
| 6,342,062 B1 | 1/2002 | Suon et al. | |
| 6,419,693 B1 * | 7/2002 | Fariabi | 623/1.18 |
| 6,666,930 B2 * | 12/2003 | Aoyama et al. | 148/306 |
| 6,767,418 B1 * | 7/2004 | Zhang et al. | 148/421 |

FOREIGN PATENT DOCUMENTS

| | | |
|---|---|---|
| WO | WO 02/078764 | 10/2002 |

OTHER PUBLICATIONS

International Search Report dated Jun. 17, 2004.

Gebeau, R. C. et al., "Biomedical implant alloy", Advanced Materials & Processes, Sep. 2001. vol. 159, No. 9, pp. 46-48.

Zhong et al., "Biodegradable Implantable or Insertable Medical Devices with Controlled Change of Physical Properties Leading to Biomechanical Compatibility". U.S. Appl. No. 09/895,415, filed Jul. 2, 2001.

Radsich et al., "Radiopaque Stent", U.S. Appl. No. 09/823,308, filed Mar. 30, 2001.

* cited by examiner

Elemental Composition (wt. %)

| Alloy | Ni | Cr | Mn | C | Mo | Si | N | Co | Pt | Ru | Pd | Ir | Cu | Fe |
|---|---|---|---|---|---|---|---|---|---|---|---|---|---|---|
| Alloy A | 0 | 16 | 8 | 0.03 | 2.3 | 0.2 | 0.16 | 0.07 | 6 | 1.5 | 0 | 0 | 2 | Balance |
| Alloy B | 0 | 16 | 8 | 0.03 | 2.3 | 0.2 | 0.16 | 0.07 | 6 | 0 | 1 | 0 | 2 | Balance |
| Alloy C | 0 | 16 | 8 | 0.03 | 2.3 | 0.2 | 0.16 | 0.07 | 0 | 1.5 | 0 | 6 | 2 | Balance |
| Alloy D | 0 | 16 | 8 | 0.03 | 2.3 | 0.2 | 0.16 | 0.07 | 0 | 0 | 1.5 | 6 | 2 | Balance |

FIG. 2A

| Alloy | Cr Equivalent | Ni Equivalent | $Cr_{eq}/Ni_{eq}$ |
|---|---|---|---|
| Alloy A | 19.0 | 13.8 | 1.38 |
| Alloy B | 19.0 | 13.6 | 1.40 |
| Alloy C | 19.0 | 13.5 | 1.41 |
| Alloy D | 19.0 | 13.4 | 1.41 |

FIG. 2B

| Alloy | As Cast Microstructure | | | New PHACOMP Analysis (Annealing Temp = 1050°C) | | | | |
|---|---|---|---|---|---|---|---|---|
| | % δ (DeLong) | Mode | $M_d$ Temp (°C) | $Cr_2N$ Phase | σ Phase | $Md^{ave}$ (eV) | $Md^{crit}$ (eV) | Max N Sol. (%) |
| Alloy A | 1 | AF | -115.2 | No | No | 0.920 | 0.925 (2) | 0.41 |
| Alloy B | 2 | AF/FA | -110.2 | No | No | 0.918 | 0.924 (2) | 0.39 |
| Alloy C | 2 | AF/FA | -115.2 | No | No | 0.923 | 0.926 (2) | 0.44 |
| Alloy D | 2 | AF/FA | -115.2 | No | No | 0.921 | 0.925 (2) | 0.42 |

FIG. 2C

| Alloy | Mechanical (Annealed - 1050°C) | | Corrosion | Radiopacity Change from 316LS (Thickness = 0.005") | | | |
|---|---|---|---|---|---|---|---|
| | Yield Strength (MPa) | UTS (MPa) | PRE | 40 keV (%) | 60 keV (%) | 80 keV (%) | 100 keV (%) |
| Alloy A | 376 | 734 | 26.2 | +6.4 | +2.2 | +5.3 | +3.0 |
| Alloy B | 376 | 716 | 26.2 | +5.9 | +2.1 | +5.2 | +2.9 |
| Alloy C | 376 | 722 | 26.2 | +6.1 | +2.1 | +5.2 | +2.9 |
| Alloy D | 376 | 710 | 26.2 | +6.4 | +2.2 | +5.2 | +2.9 |

FIG. 2D

Elemental Composition (wt. %)

| Alloy | Ni | Cr | Mn | C | Mo | Si | N | Co | Pt | Ru | Pd | Ir | Cu | Fe |
|---|---|---|---|---|---|---|---|---|---|---|---|---|---|---|
| Alloy E | 0 | 17 | 8 | 0.03 | 2.6 | 0.2 | 0.22 | 0.07 | 6 | 0 | 0 | 0 | 2 | Balance |
| Alloy F | 0 | 17 | 8 | 0.03 | 2.6 | 0.2 | 0.22 | 0.07 | 0 | 0 | 0 | 6 | 2 | Balance |
| Alloy G | 0 | 18 | 1.5 | 0.03 | 2.8 | 0.2 | 0.06 | 24 | 6 | 0 | 0 | 0 | 0.09 | Balance |
| Alloy H | 0 | 18 | 1.5 | 0.03 | 2.8 | 0.2 | 0.06 | 24 | 0 | 0 | 0 | 6 | 0.09 | Balance |
| Alloy I | 0 | 18 | 1.5 | 0.03 | 2.8 | 0.2 | 0.06 | 17 | 12.5 | 0 | 0 | 0 | 0.09 | Balance |
| Alloy J | 0 | 17 | 6 | 0.03 | 2.6 | 0.2 | 0.16 | 0.07 | 12.5 | 0 | 0 | 0 | 2 | Balance |
| Alloy K | 0 | 17 | 6 | 0.03 | 2.6 | 0.2 | 0.16 | 0.07 | 0 | 0 | 0 | 12.5 | 2 | Balance |

FIG. 3A

| Alloy | Cr Equivalent | Ni Equivalent | $Cr_{eq}/Ni_{eq}$ |
|---|---|---|---|
| Alloy E | 20.3 | 15.0 | 1.35 |
| Alloy F | 20.3 | 14.7 | 1.38 |
| Alloy G | 21.5 | 16.1 | 1.33 |
| Alloy H | 21.5 | 15.8 | 1.36 |
| Alloy I | 21.5 | 16.3 | 1.32 |
| Alloy J | 20.3 | 15.3 | 1.33 |
| Alloy K | 20.3 | 14.6 | 1.39 |

| Alloy | As Cast Microstructure | | | New PHACOMP Analysis (Annealing Temp = 1050°C) | | | | |
|---|---|---|---|---|---|---|---|---|
| | % δ (DeLong) | Mode | $M_d$ Temp (°C) | $Cr_2N$ Phase | σ Phase | $Md^{ave}$ (eV) | $Md^{crit}$ (eV) | Max N Sol. (%) |
| Alloy E | 2 | AF | -147.1 | No | No | 0.921 | 0.925 (2) | 0.42 |
| Alloy F | 3 | AF | -147.1 | No | No | 0.923 | 0.926 (2) | 0.45 |
| Alloy G | 4 | AF | -2.6 | No | No | 0.910 | 0.917 (1) | 0.30 |
| Alloy H | 5 | AF | -2.6 | No | No | 0.912 | 0.917 (1) | 0.33 |
| Alloy I | 3 | AF | -67.6 | No | Borderline* | 0.916 | 0.917 (1) | 0.37 |
| Alloy J | 2 | AF | -168.2 | No | No | 0.922 | 0.925 (2) | 0.43 |
| Alloy K | 4 | AF/FA | -168.2 | No | Borderline* | 0.928 | 0.927 (2) | 0.51 |

| Alloy | Mechanical (Annealed – 1050°C) | | Corrosion | Radiopacity Change from 316LS (Thickness = 0.005") | | | |
|---|---|---|---|---|---|---|---|
| | Yield Strength (MPa) | UTS (MPa) | PRE | 40 keV (%) | 60 keV (%) | 80 keV (%) | 100 keV (%) |
| Alloy E | 406 | 744 | 29.1 | +4.6 | +1.6 | +5.0 | +2.8 |
| Alloy F | 406 | 732 | 29.1 | +4.3 | +1.6 | +4.9 | +2.7 |
| Alloy G | 307 | 651 | 28.2 | +7.0 | +2.4 | +5.5 | +3.1 |
| Alloy H | 307 | 639 | 28.2 | +6.8 | +2.3 | +5.4 | +3.0 |
| Alloy I | 307 | 710 | 28.2 | +15.5 | +5.2 | +12.2 | +6.8 |
| Alloy J | 378 | 767 | 28.1 | +13.5 | +4.6 | +11.7 | +6.5 |
| Alloy K | 378 | 742 | 28.1 | +12.9 | +4.4 | +11.5 | +6.3 |

| Alloy | Elemental Composition (wt %) | | | | | | | | | | | | | | |
|---|---|---|---|---|---|---|---|---|---|---|---|---|---|---|---|
| | Ni | Cr | Mn | C | Mo | Si | N | Co | Pt | Ru | Pd | Ir | Rh | Au | Cu | Fe |
| Alloy L | 0 | 18 | 1.5 | 0.03 | 2.8 | 0.2 | 0.06 | 10 | 25 | 0 | 0 | 0 | 0 | 0 | 0.09 | Balance |
| Alloy M | 0 | 18 | 1.5 | 0.03 | 2.8 | 0.2 | 0.06 | 12.5 | 22.5 | 0 | 0 | 0 | 0 | 0 | 0.09 | Balance |
| Alloy N | 0 | 18 | 1.5 | 0.03 | 2.8 | 0.2 | 0.06 | 15 | 20 | 0 | 0 | 0 | 0 | 0 | 0.09 | Balance |
| Alloy O | 0 | 18 | 1.5 | 0.03 | 2.8 | 0.2 | 0.06 | 17.5 | 17.5 | 0 | 0 | 0 | 0 | 0 | 0.09 | Balance |
| Alloy P | 0 | 18 | 1.5 | 0.03 | 2.8 | 0.2 | 0.06 | 20 | 15 | 0 | 0 | 0 | 0 | 0 | 0.09 | Balance |
| Alloy Q | 0 | 18 | 1.5 | 0.03 | 2.8 | 0.2 | 0.06 | 22.5 | 12.5 | 0 | 0 | 0 | 0 | 0 | 0.09 | Balance |

FIG. 4A

| Alloy | Cr Equivalent | Ni Equivalent | $Cr_{eq}/Ni_{eq}$ |
|---|---|---|---|
| Alloy L | 21.5 | 18.7 | 1.15 |
| Alloy M | 21.5 | 18.6 | 1.16 |
| Alloy N | 21.5 | 18.4 | 1.16 |
| Alloy O | 21.5 | 18.3 | 1.17 |
| Alloy P | 21.5 | 18.3 | 1.18 |
| Alloy Q | 21.5 | 18.1 | 1.19 |

| Alloy | As Cast Microstructure | | | New PHACOMP Analysis (Annealing Temp = 1050°C) | | | | |
|---|---|---|---|---|---|---|---|---|
| | % δ (DeLong) | Mode | $M_d$ Temp (°C) | $Cr_2N$ Phase | σ Phase | $Md^{ave}$ (eV) | $Md^{crit}$ (eV) | Max N Sol. (%) |
| Alloy L | 0 | A | -192.6 | No | Yes | 0.925 | 0.917 (1) | 0.47 |
| Alloy M | 0 | A | -167.6 | No | Yes | 0.922 | 0.917 (1) | 0.43 |
| Alloy N | 0 | A | -142.6 | No | Borderline | 0.919 | 0.917 (1) | 0.40 |
| Alloy O | 0 | A | -117.6 | No | Borderline | 0.917 | 0.917 (1) | 0.37 |
| Alloy P | 0 | A | -92.6 | No | No | 0.914 | 0.917 (1) | 0.34 |
| Alloy Q | 0 | A | -67.6 | No | No | 0.912 | 0.917 (1) | 0.32 |

FIG. 4D

| Alloy | Mechanical (Annealed-1050 °C) | | Corrosion | Radiopacity Change from 316LS (Thickness = 0.005") | | | |
|---|---|---|---|---|---|---|---|
| | Yield Strength (MPa) | UTS (MPa) | PRE | 40 keV % | 60 keV % | 80 keV % | 100 keV % |
| Alloy L | 307 | 822 | 28.2 | 37.2 | 11.8 | 28.3 | 15.3 |
| Alloy M | 307 | 800 | 28.2 | 32.4 | 10.4 | 24.7 | 13.4 |
| Alloy N | 307 | 777 | 28.2 | 28.0 | 9.1 | 21.4 | 11.7 |
| Alloy O | 307 | 755 | 28.2 | 23.8 | 7.8 | 18.2 | 10.0 |
| Alloy P | 307 | 732 | 28.2 | 19.9 | 6.6 | 15.2 | 8.4 |
| Alloy Q | 307 | 710 | 28.2 | 16.2 | 5.4 | 12.3 | 6.9 |

MEDICAL DEVICES

TECHNICAL FIELD

The invention relates to medical devices, such as, for example, stents and stent-grafts.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon expandable endoprosthesis. The balloon can be inflated to deform and to fix the expanded endoprosthesis at a predetermined position in contact with the lumen wall. The balloon can then be deflated, and the catheter withdrawn.

In another technique, a self-expandable endoprosthesis is formed of an elastic material that can be reversibly compacted and expanded, e.g., elastically or through a material phase transition. During introduction into the body, the endoprosthesis is restrained in a compacted condition on a catheter. Upon reaching the desired implantation site, the restraint is removed, for example, by retracting a restraining device such as an outer sheath, enabling the endoprosthesis to self-expand by its own internal elastic restoring force.

To support a passageway open, endoprostheses are made of materials, such as low-carbon, austenitic stainless steel or Nitinol (a nickel-titanium alloy), having appropriate mechanical properties, such as tensile strength and yield strength. An example of a suitable stainless steel is UNS S31673, which is similar to AISI 316L but having a higher chromium and nickel content range. UNS S 31673 has a general composition shown in Table 1:

TABLE 1

Composition of UNS S31673

| Element | Weight Percent |
| --- | --- |
| Carbon | 0.030 maximum |
| Manganese | 2.00 maximum |
| Phosphorus | 0.025 maximum |
| Sulfur | 0.010 maximum |
| Silicon | 0.75 maximum |
| Chromium | 17.00 to 19.00 |
| Nickel | 13.00 to 15.00 |
| Molybdenum | 2.25 to 3.00 |
| Nitrogen | 0.10 maximum |
| Copper | 0.50 maximum |
| Iron | Balance | where the chemical composition is maintained such that % Cr+(3.3)(X % Mo)≧26.0. Materials such as UNS S31673, however, can be relatively radiolucent. That is, the materials may not be easily visible under X-ray fluoroscopy, a technique used to locate and to monitor the endoprostheses during and after delivery. To enhance their visibility (e.g., by increasing their radiopacity), the endoprostheses can include a relatively radiopaque material, such as gold or platinum.

SUMMARY

The invention relates to medical devices, such as, for example, stents and stent-grafts. In one aspect, the invention features a medical device including an austenitic and non-magnetic stainless steel alloy that includes a small quantity amount of nickel. For example, in some embodiments, the alloy is substantially free of nickel, which, as used herein, means that the alloy has less than about one weight percent of nickel. Nickel can cause an adverse (e.g., allergic and/or cytotoxic) effect in some subjects. At the same time, the alloy can provide the medical device with good radiopacity, tensile strength, yield strength, elongation, and/or resistance to corrosion. In some cases, the alloy has a radiopacity, physical properties, and mechanical properties comparable or better than those of UNS S31673.

In another aspect, the invention features a medical device having an alloy including iron and chromium, being substantially free of nickel, and having a radiopacity greater than the radiopacity of UNS S31673.

In another aspect, the invention features a medical device having an alloy including iron, chromium, and less than five weight percent of nickel. The alloy is fully austenitic and has a radiopacity greater than the radiopacity of UNS S31673. The alloy can have less than five weight percent of nickel, e.g., less than four, three, two, or one weight percent of nickel.

Embodiments may include one or more of the following features. The alloy is fully austenitic. The alloy, after annealing, has a tensile strength greater than about 490 MPa. The alloy, after annealing, has a yield strength of greater than about 190 MPa. The device alloy has a pitting resistance equivalent greater than about 26. The alloy further includes one or more elements selected from platinum, ruthenium, palladium, iridium, rhodium, gold, and/or osmium. The alloy includes between about 0.5% and about 40% by weight of the first element. The device is in the form of a stent.

The alloy can have one or more of the following compositions. The alloy includes between about 0.01% and about 1.0% by weight percent of nitrogen, e.g., less than about 1.0% by weight of nitrogen. The alloy includes between about 0.07% and about 55% by weight of cobalt, e.g., between about 0.07% and about 32% by weight of cobalt. The alloy includes between about 0.5% and about 20% by weight of manganese. The alloy includes between about 0.03% and about 6% by weight of copper. The alloy includes less than about 30% by weight of chromium, e.g., less than about 20% by weight of chromium. The alloy includes less than about 3% by weight of molybdenum.

In another aspect, the invention features a medical device having an alloy including iron, less than about 30% by weight of chromium, less than about 3% by weight of molybdenum, less than about 55% by weight of cobalt, less than about 20% by weight of manganese, less than about 6% by weight of copper, less than about 0.03% by weight of nickel, less than about 1.0% by weight of nitrogen, and between about 0.5% and about 40% by weight of a first element selected from platinum, ruthenium, palladium, iridium, rhodium, gold, and/or osmium, wherein the alloy is substantially austenitic.

The alloy can have one or more of the following compositions. The alloy includes between about 0.01% and 1.0% by weight of nitrogen. The alloy includes between about 0.07% and about 32% by weight of cobalt. The alloy includes between about 0.5% and about 20% by weight of manganese. The alloy includes between about 0.03% and about 6% by weight of copper.

In another aspect, the invention features a method of making a medical device. The method includes selecting an alloy including iron, chromium, and less than 5% by weight of nickel, wherein the alloy is substantially austenitic and has at least one of the following properties: a radiopacity greater than the radiopacity of UNS S31673, a tensile strength, after annealing, greater than about 490 MPa, a yield strength, after annealing, greater than about 190 MPa, or a pitting resistance equivalent greater than about 26; and incorporating the alloy in the medical device, such as a stent.

The alloy can have at least two of the properties, e.g., at least three of the properties. The alloy can be substantially free of nickel. The alloy can include between about 0.5% and about 40% by weight of a first element selected from platinum, ruthenium, palladium, iridium, rhodium, gold, or osmium.

In another aspect, the invention features a medical device including a nickel-free alloy having the same structure (e.g., face centered cubic) and comparable mechanical properties as a stainless steel, such as UNS S31673, conforming to ASTM F 138, F 139, and ISO 5832-1 Composition D. The alloy can have enhanced radiopacity.

The alloys described herein can also be used in dental prostheses, jewelry, flatware, or other items that can come into bodily contact.

In yet another aspect, the invention features the alloy compositions described herein.

Other aspects, features, and advantages of the invention will be apparent from the description of the preferred embodiments thereof and from the claims.

DESCRIPTION OF DRAWINGS

FIG. 2A is a table showing the chemical compositions of four alloys; FIG. 2B is a table showing the $Cr_{eq}$, $Ni_{eq}$, and $Cr_{eq}/Ni_{eq}$ ratios of the alloys of FIG. 2A; FIG. 2C is a table showing the microstructure and New PHACOMP calculations for the alloys of FIG. 2A; and FIG. 2D is a table showing the calculated mechanical, corrosion, and radiopacity properties of the alloys of FIG. 2A.

FIG. 3A is a table showing the chemical compositions of six alloys; FIG. 3B is a table showing the $Cr_{eq}$, $Ni_{eq}$, and $Cr_{eq}/Ni_{eq}$ ratios of the alloys of FIG. 3A; FIG. 3C is a table showing the microstructure and New PHACOMP calculations for the alloys of FIG. 3A; and FIG. 3D is a table showing the calculated mechanical, corrosion, and radiopacity properties of the alloys of FIG. 3A.

FIG. 4A is a table showing the chemical compositions of six alloys; FIG. 4B is a table showing the $Cr_{eq}$, $Ni_{eq}$, and $Cr_{eq}/Ni_{eq}$ ratios of the alloys of FIG. 4A; FIG. 4C is a table showing the microstructure and New PHACOMP calculations for the alloys of FIG. 4A; and FIG. 4D is a table showing the calculated mechanical, corrosion, and radiopacity properties of the alloys of FIG. 4A

DETAILED DESCRIPTION

Figure 1:
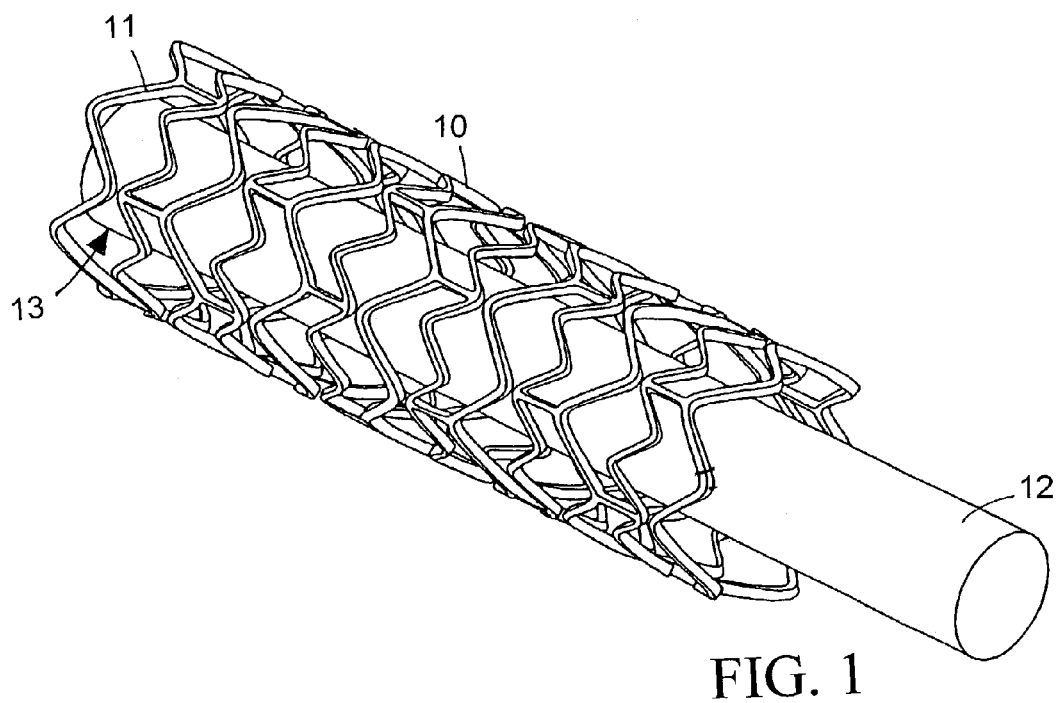
FIG. 1 is a perspective view of an embodiment of a stent.

Referring to FIG. 1, a support 12 carries a stent 10, which is the form of a tubular member including struts 11 and openings 13. Depending on the type of stent, e.g., balloon-expandable or self-expandable, support 12 can be a balloon catheter or a catheter shaft.

Stent 10 is composed of an alloy based on an iron-chromium stainless steel. As shown in Table 2, the alloy generally includes, among others, a small quantity of nickel, chromium, iron, and an element X:

TABLE 2

Composition of alloy of stent 10

| Element | Weight Percent |
| --- | --- |
| Nickel | $\leq 5.0$ |
| Chromium | 15.00-20.00 |
| Element X | 0.50-40.00 |
| Iron | balance (e.g., 40-65) |

Element X can include one or more (e.g., two, three, four, five, six or more) of the following elements, in any combination: platinum, ruthenium, palladium, iridium, rhodium, gold, and osmium. In addition, the alloy may include one or more of the following elements: carbon, nitrogen, manganese, copper, cobalt, and molybdenum.

As shown in Table 2, the alloy of stent 10 has a small quantity of nickel. In embodiments, the alloy has less than about five percent by weight of nickel. For example, the alloy can have less than or equal to 4%, 3%, 2%, or 1% by weight of nickel; and/or greater than or equal to 1%, 2%, 3%, or 4% by weight of nickel. Preferably, the alloy is substantially free of nickel, i.e., having less than or equal to 1% by weight of nickel (e.g., less than or equal to 0.05 or 0.03% by weight). It is believed that nickel can cause an allergic and/or cytotoxic effect in certain subjects. Therefore, by reducing the amount of nickel in the alloy of stent 10, the occurrence of the effect(s) can be reduced (e.g., minimized or eliminated).

Nickel can be used to promote a stable austenitic microstructure in a stainless steel alloy. It is believed that the austenite (face centered cubic) structure provides the alloy that is non-magnetic with good strength and ductility, which, for example, is beneficial to stent 10 because the stent can undergo considerable deformation during use. Thus, since the amount of nickel is relatively small, one or more other elements capable of promoting and/or stabilizing an austenitic microstructure ("austenitizing elements") can be added to provide a stable austenitic structure in the alloy of stent 10.

Austenitizing elements include, for example, carbon, nitrogen, manganese, copper, cobalt, and certain element X (e.g., Pt, Ir, Rh, Ru, Os, and Pd). Carbon is capable of promoting and stabilizing austenite, but at high concentrations, carbon can react to form carbides, such as iron carbides, chromium carbides, and/or molybdenum carbides. The alloy can include up to 0.03 weight percent of carbon, e.g., less than or equal to about 0.02 or 0.01 weight percent. The alloy can include greater than zero weight percent and less than about one weight percent of nitrogen, e.g., less than or equal to about 0.75, 0.50, or 0.25 weight percent. Manganese can compose up to about 20 weight percent of the alloy, e.g., less than or equal to about 15, 10, or 5 weight percent. In embodiments, such as when the alloy is used in balloon-expandable stents, the amounts of nitrogen and/or manganese are controlled so as to not significantly increase the strength, e.g., yield strength, which can hinder use of the stent. Copper, which can be an austenite promoter and/or stabilizer, can be included up to six weight percent, e.g., less than or equal to about five, four, three, two, or one weight percent. Cobalt, which can be an austenite promoter and/or stabilizer can be includes up to 55 weight percent, e.g., less than or equal about 55, 50, 45, 40, 35, 32, 30, 25, 20, 15, 10 or 5 weight percent, and/or greater than or equal to about 5, 10, 15, 20, 25, 30, 32, 35, 40, 45, or 50 weight percent. In some cases, the alloy includes less than one weight percent of cobalt.

Molybdenum can be added to the alloy to enhance the resistance of the alloy to corrosion, e.g., pitting and crevice corrosion. In embodiments, the alloy includes between about 2.25 to about 3.00 weight percent of molybdenum, e.g., greater than or equal to 2.3, 2.4, 2.5, 2.6, 2.7, 2.8, or 2.9 weight percent, and/or less than or equal to 3.0, 2.9, 2.8, 2.7, 2.6, 2.5, 2.4, or 2.3 weight percent.

Chromium can also be added to the alloy to make the alloy more corrosion resistant. In embodiments, at 12 wt % or higher, chromium can form a thin oxide layer on the surface of a steel that enhances the resistance of the steel to corrosive attack. The degree of corrosion resistance is a function of the chromium concentration and the concentrations of other elements in the steel. The alloy can include between about 5 and about 30 weight percent of chromium. The alloy can include greater than or equal to 5, 8, 11, 14, 17, 20, 25, or 30 weight percent, and/or less than or equal to 30, 25, 20, 17, 14, 11, or 8 weight percent of chromium. Increasing the concentration of chromium can improve the pitting resistance, e.g., to be equal to or better than UNS S31673. But in some cases, the higher the chromium concentration, the more austenitizing elements and/or stabilizers, such as Co, Mn, N, and/or Cu, may be required to maintain an austenitic structure.

Element X is selected from a group of elements capable of enhancing the radiopacity of the alloy. Element X can be a face-centered-cubic element. In embodiments, element X has a density equal to or greater than about 2 g/cc, e.g., equal to or greater than 9.9 g/cc. The alloy can include between about 0.5 and about 40 weight percent of element X. The alloy can include greater than or equal to about 5, 10, 15, 20, 25, 30, or 35 weight percent, and/or less than or equal to about 40, 35, 30, 25, 20, 15, 10, or 5 weight percent of element X. In some cases, such as when element X is rhodium, iridium, palladium, ruthenium, osmium, or platinum, element X can also promote and/or stabilize the austenite structure.

The alloy can include residual amounts of impurities elements. For example, the alloy may include residual amounts of phosphorus (e.g:, 0.025 wt % maximum), silicon (e.g. 0.75 wt % maximum), sulfur (e.g., 0.010 wt % maximum), niobium (e.g., about 0.013 wt %), vanadium (e.g., about 0.07 wt %), titanium (e.g., 0.002 wt %), and/or aluminum (e.g., about 0.009 wt %). Other residual elements and residual amounts are possible, which can be a function of the source of the materials.

Iron makes up the balance of the alloy of stent 10, e.g., after accounting for the other elements in the alloy described above. In certain embodiments, the alloy includes between about 40 and about 65 weight percent of iron.

Particular compositions of the alloy are selected to provide the alloy with one or more selected physical and mechanical properties, such as radiopacity, strength, elongation, and resistance to corrosion, suitable for intravascular use. In embodiments, the physical and mechanical properties are comparable to or better than those of other stainless steels, such as UNS S31673, used in medical devices. Without wishing to be bound by theory, it is believed that these properties can be modeled to help predict, and therefore, target, compositions can provide the selected properties. For example, a particular composition can be analyzed to determine theoretically whether it can form a selected phase, such as austenite. Similarly, the composition can be modeled to determine theoretically whether is can have suitable mechanical and physical properties for medical applications.

Microstructure: In some embodiments, the alloy has a microstructure that is predominantly (greater than 50%) austenitic, i.e., the alloy is formed predominantly of the austenite phase. For example, the alloy can be equal to or greater than 80%, 85%, 90%, or 95% austenitic. Preferably, the alloy is fully austenitic. As discussed above, it is believed that the austenite structure can provide a non-magnetic alloy with good strength and ductility, e.g., suitable for stent applications.

The microstructure of an alloy can be predicted using constitutional diagrams, such as the Schaeffler diagram and the Welding Research Council (WRC-1988) diagram. (See ASM International, ASM Speciality Handbook: Stainless Steels, Welding, pp. 340-342, Davis J. R. Library on Congress Cataloging-In-Publication Data, 1994; Siewert et al., Ferrite Number Prediction to 100FN in Stainless Steel Weld Metal, Weld. J., Vol. 67 No. 12, 1988, pp. 289s-298s; and Hull, Delta Ferrite and Martensite Formation in Stainless Steels, Welding Research Supplement, May 1973, pp. 193-203.) The Schaeffler diagram predicts the phases in the alloy, and the WRC diagram provides more detail in the range under consideration. In particular, the phase to which the alloy solidifies can be dependent on the chromium equivalent to nickel equivalent ratio ($Cr_{eq}/Ni_{eq}$), in which:

$$Cr_{eq} = (\% \text{ Cr}) + (\% \text{ Mo}) + (1.5)(\% \text{ Si}) + (0.5)(\% \text{ Nb})$$

$$Ni_{eq} = (\% \text{ Ni}) + (30)(\% \text{ C}) + (0.5)(\% \text{ Mn})$$

For a $Cr_{eq}/Ni_{eq}$ ratio approximately 1.48 or less, the composition can solidify as austenite; for a $Cr_{eq}/Ni_{eq}$ ratio approximately between 1.48 and 1.95, the composition can solidify as a duplex structure of austenite and ferrite; and for a $Cr_{eq}/Ni_{eq}$ ratio approximately 1.95 or greater, the composition can solidify as ferrite. In embodiments, it is desirable for the composition to solidify in the austenite (A) phase or the austenite-ferrite (AF) phase, which is mostly austenite. In the ferrite (F) phase or ferrite-austenite (FA) phase (which is mostly ferrite), the solubility of nitrogen (which can increase austenite formation and stability) can decrease as the composition solidifies, resulting in increased porosity.

Austenite stability at ambient temperature can also reduce the occurrence of martensite formation in the alloy during cold forming operations. Uncontrolled transformation of austenite to martensite can make the alloy magnetic, can lead to dimensional instability, and can be the dominant cause of work hardening, e.g., reduced ductility. The martensite deformation temperature, $M_d$, can be the temperature at which 50% of martensite is formed by 30% deformation. $M_d$ can be calculated as follows:

$$M_d(°C.) = 13 - 462(C+N) - 9.2Si - 8.1Mn - 13.7Cr - 9.5Ni - 18.5Mo - 18.5Cu - 10(Ru+Rh+Pd+Ir+Pt+Au)$$

For more information, see Angel T., Formation of Martensite in Austenitic Stainless Steels: Effects of Deformation, Temperature, and Composition, Journal of the Iron and Steel Institute, May 1954, pp. 165-174. In embodiments, the austenite phase in the alloy is stable at high and low temperatures, and the formation of the intermetallic phases at grain boundaries is reduced (e.g. minimized). In certain embodiments, $M_d$ is well below zero degrees Celsius.

TCP Phases and Nitrogen Concentration: In embodiments, the alloy includes reduced (e.g., minimal or no) amounts of brittle topologically close packed (TCP) phases. A phase computational methodology, called "New PHA-COMP" (Morinaga et al., Solid Solubilities in Transition-Metal-Base FCC Alloys, Philosophical Magazine A, 1985, Vol. 51, No. 2, pp. 223-246), can be used to help predict the tendency of austenite to precipitate TCP phases, e.g., sigma (σ) phases in nickel-based alloys, and cobalt and iron based superalloys.

In New PHACOMP, the d orbital energy level (Md) of an element is used to calculate the average Md ($Md^{ave}$) for the composition using the formula:

$$Md^{ave}(eV) = \Sigma X_i \cdot (Md)_i$$

where $X_i$ is the atomic fraction of element i in the composition, and $(Md)_i$ is the Md of element i. The summation is taken over all the elements of the alloy.

It is believed that when $Md^{ave}$ becomes larger than a critical value ($Md^{crit}$), phase instability can occur and a second phase, i.e., a TCP phase, is formed in the austenite matrix. $Md^{crit}$ is a function of the second phase. Here, for compositions containing ≦0.06% nitrogen:

$$Md^{crit}(eV) = 0.834 + (6.25 \times 10^{-5})T$$

where T is the temperature in Kelvin. For compositions containing >0.06% nitrogen:

$$Md^{crit}(eV) = 0.834 + (6.25 \times 10^{-5})T + 0.02 N_{max}$$

More information can be found in Uggowitzer et al., High Nitrogen Austenitic Stainless Steels—Properties and New Developments, Innovation Stainless Steel, Florence, Italy, 11-14 October 1993.

In embodiments, the alloy has an $Md^{ave}$ value equal to or greater than $Md^{crit}$, e.g., greater than by 0.002 eV.

In addition, New PHACOMP can be used to predict precipitation of chromium nitride in relatively high-nitrogen stainless steels (e.g., as described in Uggowitzer et al.). As discussed above, nitrogen can be added to austenitic steels to stabilize austenite, e.g., by reducing the occurrence of ferrite formation at high temperatures and martensitic transformation at low temperatures. In certain cases, when the nitrogen content exceeds its solubility limit in austenite, chromium nitride (e.g., $Cr_2N$) can precipitate and deplete the matrix of chromium, thereby reducing passivity.

The $Md^{ave}$ value (above) can be used to calculate this solubility limit. The solubility of nitrogen in the austenite phase can vary, e.g., as a function of the composition. In embodiments, the estimated solubility limit at annealing temperatures (e.g., about 1050° C.) is similar to that obtained after quenching. A formula to predict the maximum amount of nitrogen that can dissolve in austenite before chromium nitride precipitates, $N_{max}$(%), is:

$$N_{max}(\%) = 0.003 \exp\{41660[(Md^{ave} - 0.75)/(2765 - T)]\}$$

where T is the temperature in Kelvin. More information can be found at Uggowitzer et al. In certain embodiments, the alloy has a nitrogen concentration equal to or less than $N_{max}$(%) to reduce the occurrence of chromium nitride precipitation.

Radiopacity: The alloy is preferably radiopaque. The radiopacity of the alloy can be enhanced by including one or more element X (e.g., Pt, Ir, Os, Re, Rh, Pd, Ru, and Au). Element(s) X that are good austenite formers can also reduce the amount of other austenite forming or stabilizing elements (see above).

The effect of an element on the radiopacity of an alloy is dependent on the relative proportion of the element, and the mass attenuation coefficient of the element. The mass attenuation coefficient (μ/ρ) for each element at various energy levels can be obtained from http://physics.nist.gov/. (See, e.g., Hubbell, J. H. and Seltzer, S. M. (1997). *Tables of X-Ray Mass Attenuation Coefficients and Mass Energy-Absorption Coefficients* (version 1.03), available at http://physics.nist.gov/xaamdi [2002, Nov. 5]. National Institute of Standards and Technology, Gaithersburg, Md., which was originally published as NISTIR 5632, National Institute of Standards and Technology, Gaithersburg, Md. (1995). See, also, NISTIR 5632, Tables of X-Ray Mass Attenuation Coefficients and Mass Energy-Absorption Coefficients 1 keV to 20 MeV for Elements Z=1 to 92 and 48 Additional Substances of Dosimetric Interest, Published date: May 1995.)

The linear attenuation coefficient of an element, at a certain energy level, can be derived by multiplying its mass attenuation coefficient by its density. The average mass attenuation coefficient $(\mu/\rho)_{ave}$ of an alloy can be obtained by multiplying the elemental mass attenuation coefficient (μ/ρ) by the weight fraction of each element in the alloy, and summing the contribution of each element:

$$\left(\frac{\mu}{\rho}\right)_{ave} = \sum_{i=1}^{n} (\text{wt }\%)_i \cdot \left(\frac{\mu}{\rho}\right)_i$$

The average density for the alloy can be calculated as:

$$\frac{1}{\rho} = \sum_i \left(\frac{c_i}{\rho_i}\right)$$

where $c_i$ is the mass percent of element i, and $\rho_i$ is the density of pure element i.

The average linear attenuation coefficient $(\mu)_{ave}$ for the alloy can then be obtained by multiplying the average mass attenuation coefficient by the average density. The radiopacity at a certain energy level can be derived as:

$$\text{Radiopacity} = e^{\mu_{ave} x}$$

where $\mu_{ave}$ is the average linear attenuation coefficient, and x is the thickness of the alloy. Methods of calculating the radiopacity of an alloy at a certain energy level are also described in Craig et al., Development of a Platinum-Enhanced Radiopaque Stainless Steel (PERSS®), Stainless Steel for Medical and Surgical Applications, ASTM STP 1438, G. L. Winters and M. J. Nutts, Eds., ASTM International, Pittsburgh, Pa., 2002.

The radiopacity of the alloy is dependent on the incident energy and the thickness of the alloy. In embodiments, for an alloy sample, 0.005" (0.127 mm) thick, at an incident energy level of 40 keV, the alloy of stent 10 has a radiopacity of equal to or greater than about 1.539. At an incident energy level of 60 keV, the alloy of stent 10 can have a radiopacity of equal to or greater than about 1.156. At an incident energy level of 80 keV, the alloy of stent 10 can have a radiopacity of equal to or greater than about 1.118. At an incident energy level of 100 keV, the alloy of stent 10 can have a radiopacity of equal to or greater than about 1.069

For purposes of comparison, a stainless steel, such as UNS S31673 (0.005" thick"), has a radiopacity of 1.475 at 40 keV, 1.138 at 60 keV, 1.066 at 80 keV, and 1.040 at 100 keV. These values are median values and can vary, depending on the particular composition.

In some embodiments, the alloy has a radiopacity greater than or equal to about 105%, 110%, 115%, 120%, or 125% of the radiopacity of UNS S31673 at 80 keV for a thickness of 0.005 inch; and/or less than or equal to about 130%, 125%, 120%, 115%, 110%, or 105% of the radiopacity of UNS S31673 at 80 keV for a thickness of 0.005 inch.

Mechanical Properties: The mechanical properties of an alloy can be estimated as follows.

Tensile strength $(MPa)=470+600(N+0.02)+14Mo+ 1.5\delta+8d^{-0.5}+20Ru+7Rh+9Pt+7Ir+12Pd+5Au$ Yield strength $(MPa)=120+210(N+0.02)-0.5+2Cr+ 2Mn+14Mo+10Cu+\delta(6.15-0.054\delta)+(7+35(N+ 0.02))d^{-0.5}$ where d is the grain size (in mm), and $\delta$ is the delta ferrite content (in volume percent). In embodiments, d can be set at 0.04 mm and $\delta$ can be set at zero percent. For more information, see Nordberg, Mechanical Properties of Austenitic and Duplex Stainless Steels, Innovation Stainless Steel, Florence, Italy, 11-14 Oct. 1993, Vol. 2, pp. 2.217-2.229; and Uggowitzer et al., Strengthening of Austenitic Stainless Steels by Nitrogen, HNS-88.

In some embodiments, the alloy (after annealing) has a tensile strength of equal to or greater than 490 MPa, e.g., greater than about 500, 600, 700, or 800 MPa. Alternatively or in addition, the alloy (after annealing) can have a yield strength of equal to or greater/less than 190 MPa, e.g., greater than about 200, 300, or 400 MPa. Alternatively or in addition, the alloy (after annealing) can have an elongation equal to or greater than about 40%.

Corrosion Resistance: The corrosion resistance properties can also be estimated. In embodiments, a pitting resistance equivalent (PRE) of an alloy is greater than or equal to 26 (e.g., for ASTM F 138 and 139, and ISO5832-1). The pitting resistance equivalent can be predicted by using the formula:

$PRE=Cr+3.3Mo+16N$ which accounts for the effect of nitrogen, which can have a beneficial effect on pitting resistance. More information can be found in Gunn, Duplex Stainless Steels, Woodhead Publishing Limited, England, 1997, pp. 84.

In embodiments, the alloy has a pitting resistance equivalent equal to or greater than about 26.

By using the models and methodologies described above, different compositions of alloys can be studied to determine whether a composition can provide one or more selected properties. For example, the models and methodologies can be entered into a software program. A user can input a selected composition, and the program can output the predicted properties of the composition, e.g., in tabular or graphical form. The user can select those compositions having predetermined, predicted properties. The selected composition can have one or more (e.g., two, three, four, five, or more) of the properties described above, in any combination.

The following examples are illustrative and not intended to be limiting.

EXAMPLES

FIGS. 2A-2D, 3A-3D, and 4A-D show seventeen alloy compositions (Alloys A-Q) and their physical, microstructural, and mechanical properties, predicted using the models and methodologies described above.

All of the compositions have $Cr_{eq}/Ni_{eq}$ ratios of 1.48 or less, which indicate that the compositions can solidify to a phase containing an austenite phase. All of the compositions also have low martensite deformation temperatures, $M_d$, e.g., less than zero degrees Celsius.

New PHACOMP analyses indicate all of the alloys, except Alloys I and K-O should not precipitate sigma phases (TCP phases) because $Md^{ave}$ is less than $Md^{crit}$. Alloys L and M are predicted to precipitate sigma phases. For Alloys I, K, N, and O, the tendency of the alloy to precipitate TCP phases is borderline because the difference between $Md^{ave}$ and $Md^{crit}$ is less than 0.002. New PHACOMP analyses also indicate no precipitation of chromium nitride in the alloys because the nitrogen concentrations are less than the maximum amounts of nitrogen solubility, $N_{max}$.

The predicted mechanical, corrosion, and radiopacity properties are shown in FIGS. 2D, 3D, and 4D.

Selected alloy compositions were manufactured using high-purity raw materials. The materials were melted in a button arc furnace in a water-cooled copper hearth under an argon atmosphere of approximately 0.3 of an atmospheric pressure. The materials were homogenized by melting three times, with turning between each melt. The alloys were then annealed in a vacuum furnace, at between 1050° C. and 1150° C. for about two hours.

Stent 10 can be formed by folding and welding a sheet or a foil of the alloy to provide a tube, e.g., using inert gas or electron beam methods, with appropriate protection against oxidation. The tube can then be drawn or extruded to the desired diameter, or used to fabricate a stent directly. Alternatively, a thin-walled tube of the alloy can be used. Portions of the tube can be removed to provide the strut 11/opening 13 arrangement. The portions can be removed by laser cutting, as described, for example, in U.S. Pat. No. 5,780,807. Alternatively, the portions can be removed by electrochemical machining, electrical discharge machining, abrasive cutting/grinding methods, or photoetching. Stent 10 can then be finished by electropolishing to a smooth finish, by conventional methods. Stent 10 also can be annealed. In other embodiments, stent 10 is made from a flat pattern that is then formed into a tubular shape by rolling the pattern to bring opposing edges together. The edges can then be joined, e.g., by welding.

In general, stent 10 can be of any desired shape and size (e.g., coronary stents, aortic stents, peripheral stents, gastrointestinal stents, urology stents, and neurology stents). Depending on the application, stent 10 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 10 can be balloon-expandable, self-expandable, or a combination of both (e.g., as described in U.S. Pat. No. 5,366,504).

Stent 10 can be used, e.g., delivered and expanded, according to conventional methods. Suitable catheter systems are described in, for example, Wang U.S. Pat. No. 5,195,969, and Hamlin U.S. Pat. No. 5,270,086. Suitable stents and stent delivery are also exemplified by the NIR on Ranger® system, available from Boston Scientific Scimed, Maple Grove, Minn.

OTHER EMBODIMENTS

In other embodiments, stent 10 can include and/or be attached to a biocompatible, non-porous or semi-porous polymer matrix made of polytetrafluoroethylene (PTFE), expanded PTFE, polyethylene, urethane, or polypropylene. Stent 10 can include a releasable therapeutic agent or a pharmaceutically active compound, such as described in U.S. Pat. No. 5,674,242, commonly-assigned U.S. Ser. No. 09/895,415, filed Jul. 2, 2001, and U.S. Ser. No. 10/112,391, filed Mar. 28, 2002. The therapeutic agents or pharmaceutically active compounds can include, for example, anti-thrombogenic agents, antioxidants, anti-inflammatory agents, anesthetic agents, anti-coagulants, and antibiotics.

The alloy described above can also be used in other medical devices, e.g., endoprostheses. For example, the alloy can be used in filters such as removable thrombus filters described in Kim et al., U.S. Pat. No. 6,146,404; in intravascular filters such as those described in Daniel et al., U.S. Pat. No. 6,171,327; and vena cava filters such as those described in Soon et al., U.S. Pat. No. 6,342,062.

The alloy can also be used in guidewires such as a Meier Steerable Guide Wire (for AAA stent procedure) and an ASAP Automated Biopsy System described in U.S. Pat. Nos. 4,958,625, 5,368,045, and 5,090,419.

All publications, references, websites, applications, and patents referred to herein are incorporated by reference in their entirety.

Other embodiments are within the claims.

What is claimed is:

1. An endoprosthesis, comprising:
a tubular member capable of supporting a body passageway, the tubular member being formed of a non-magnetic alloy comprising at least 40% by weight of iron, from about 5% by weight to about 20% by weight of chromium, and greater than about 5% by weight of a first element having a density greater than 9.9 g/cc, the alloy having less than or equal to 1% by weight of nickel and having a radiopacity greater than the radiopacity of UNS S31673.

2. The endoprosthesis of claim 1, wherein the alloy is fully austenitic.

3. The endoprosthesis of claim 1, wherein the radiopacity is greater than about 105% of the radiopacity of UNS S31673 at 80 keV for a thickness of 0.005 inch.

4. The endoprosthesis of claim 1, wherein the radiopacity is greater than about 110% of the radiopacity of UNS S31673 at 80 keV for a thickness of 0.005 inch.

5. The endoprosthesis of claim 1, wherein the radiopacity is greater than about 115% of the radiopacity of UNS S31673 at 80 keV for a thickness of 0.005 inch.

6. The endoprosthesis of claim 1, wherein the radiopacity is greater than about 120% of the radiopacity of UNS S31673 at 80 keV for a thickness of 0.005 inch.

7. The endoprosthesis of claim 1, wherein the radiopacity is greater than about 125% of the radiopacity of UNS S31673 at 80 keV for a thickness of 0.005 inch.

8. The endoprosthesis of claim 1, wherein the alloy, after annealing, has a tensile strength greater than about 490 MPa.

9. The endonrosthesis of claim 1, wherein the alloy, after annealing, has a yield strength of greater than about 190 MPa.

10. The endoprosthesis of claim 1, wherein the alloy has a pitting resistance equivalent greater than about 26.

11. The endoprosthesis of claim 1, wherein first element is selected from the group consisting of platinum, ruthenium, palladium, iridium, rhodium, gold, and osmium.

12. The endoprosthesis of claim 11, wherein the alloy comprises a plurality of first elements.

13. The endonrosthesis of claim 11, wherein the alloy comprises greater than about 5% by weight to about 40% by weight of the first element.

14. The endoprosthesis of claim 1, in the form of a stent.

15. An endoprosthesis, comprising:
a tubular member capable of supporting a body passageway, the tubular member being formed of a non-magnetic alloy comprising at least 40% by weight of iron, from about 5% to about 20% by weight of chromium, greater than about 5% by weight of a first element having a density greater than 9.9 g/cc, and less than four weight percent of nickel, the alloy being fully austenitic and having a radiopacity greater than the radiopacity of UNS S31673.

16. The endoprosthesis of claim 15, wherein the alloy comprises less than about three weight percent of nickel.

17. The endoprosthesis of claim 15, wherein the alloy comprises less than about one weight percent of nickel.

18. The endonrosthesis of claim 15, wherein the radiopacity is greater than about 105% of the radiopacity of UNS S31673 at 80 keV for a thickness of 0.005 inch.

19. The endoprosthesis of claim 15, wherein the radiopacity is greater than about 110% of the radiopacity of UNS S31673 at 80 keV for a thickness of 0.005 inch.

20. The endoprosthesis of claim 15, wherein the radiopacity is greater than about 115% of the radiopacity of UNS S31673 at 80 keV for a thickness of 0.005 inch.

21. The endoprosthesis of claim 15, wherein the radiopacity is greater than about 120% of the radiopacity of UNS S31673 at 80 kcV for a thickness of 0.005 inch.

22. The endoprosthesis of claim 15, wherein the radiopacity is greater than about 125% of the radiopacity of UNS S31673 at 80 keV for a thickness of 0.005 inch.

23. The endonrosthesis of claim 15, wherein the alloy further comprises between about 0.01% and about 1.0% by weight percent of nitrogen.

24. The endoprosthesis of claim 15, wherein the alloy further comprises between about 0.07% and about 55% by weight of cobalt.

25. The endoprosthesis of claim 15, wherein the alloy further comprises between about 0.07% and about 32% by weight of cobalt.

26. The endoprosthesis of claim 15, wherein the alloy further comprises between about 0.5% and about 20% by weight of manganese.

27. The endoprosthesis of claim 15, wherein the alloy further comprises between about 0.03% and about 6% by weight of copper.

28. The endoprosthesis of claim 15, wherein the first element is selected from the group consisting of platinum, ruthenium, palladium, iridium, rhodium, gold, and osmium.

29. The endoprosthesis of claim 28, wherein the alloy comprises a plurality of first elements.

30. The endoprosthesis of claim 28, wherein the alloy comprises greater than about 5% by weight to about 40% by weight of the first element.

31. The endonrosthesis of claim 15, wherein the alloy, after annealing, has a tensile strength greater than about 490 MPa.

32. The endoprosthesis of claim 15, wherein the alloy, after annealing, has a yield strength of greater than about 190 MPa.

33. The endoprosthesis of claim 15, wherein the alloy has a pitting resistance equivalent greater than about 26.

34. The endoprosthesis of claim 15, wherein the alloy comprises less than about 17% by weight of chromium.

35. The endoprosthesis of claim 15, wherein the alloy comprises less than about 14% by weight of chromium.

36. The endonrosthesis of claim 15, wherein the alloy further comprises less than about 3% by weight of molybdenum.

37. The endoDrosthesis of claim 15, wherein the alloy further comprises less than about 1.0% by weight of nitrogen.

38. The endoprosthesis of claim 15, in the form of a stent.

39. An endoprosthesis, comprising:
a tubular member capable of supporting a body passageway, the tubular member being formed of a non-magnetic alloy comprising
at least 40% by weight of iron,
between about 5% and about 30% by weight of chromium,
less than about 3% by weight of molybdenum,
less than about 55% by weight of cobalt,
less than about 20% by weight of manganese,
less than about 6% by weight of copper,
less than about 0.03% by weight of nickel,
less than about 1.0% by weight of nitrogen, and
between about 0.5% and about 40% by weight of a first element selected from a group consisting of platinum, ruthenium, palladium, iridium, rhodium, gold, and osmium,
the alloy being substantially austenitic.

40. The endoprosthesis of claim 39, in the form of a stent.

41. The endoprosthesis of claim 39, comprising a plurality of first elements.

42. The endoprosthesis of claim 39, wherein the alloy comprises between about 0.01% and 1.0% by weight of nitrogen.

43. The endoprosthesis of claim 39, wherein the alloy comprises between about 0.07% and about 32% by weight of cobalt.

44. The endoprosthesis of claim 39, wherein the alloy comprises between about 0.5% and about 20% by weight of manganese.

45. The endoprosthesis of claim 39, wherein the alloy comprises between about 0.03% and about 6% by weight of copper.

46. A method of making an endourosthesis, the method comprising:
selecting a non-magnetic alloy comprising at least 40% by weight of iron, from about 5% to about 20% by weight of chromium, greater than about 5% by weight of a first element having a density greater than 9.9 g/cc, and less than 4% by weight of nickel, the alloy being substantially austenitic and having at least one of the following properties:
(a) a radiopacity greater than the radiopacity of UNS S3 1673,
(b) a tensile strength, after annealing, greater than about 490 MPa,
(c) a yield strength, after annealing, greater than about 190 MPa, or
(d) a pitting resistance equivalent greater than about 26,
incorporating the alloy in a tubular member of the endoprosthesis, the tubular member capable of supporting a body passageway.

47. The method of claim 46, wherein the alloy has at least two of the properties.

48. The method of claim 46, wherein the alloy has at least three of the properties.

49. The method of claim 46, wherein the alloy is substantially free of nickel.

50. The method of claim 46, wherein the alloy comprises between about 0.5% and about 40% by weight of a first element selected from a group consisting of platinum, ruthenium, palladium, iridium, rhodium, gold, and osmium.

51. The method of claim 46, wherein the endoprosthesis is a stent.

52. The endoprosthesis of claim 1, wherein the alloy comprises between about 40% and about 60% by weight of iron.

53. The endoprosthesis of claim 15, wherein the alloy comprises between about 40% and about 60% by weight of iron.

54. The endoprosthesis of claim 39, wherein the alloy comprises between about 40% and about 60% by weight of iron.

55. The method of claim 46, wherein the alloy comprises between about 40% and about 60% by weight of iron.

56. The endoprosthesis of claim 1, where in the alloy comprises from about 10% by weight to about 40% by weight of the first element.

57. The endoprosthesis of claim 15, wherein the alloy comprises from about 10% by weight to about 40% by weight of the first element.

58. The endoprosthesis of claim 39, wherein the alloy comprises from about 10% by weight to about 40% by weight of the first element.

59. The endoprosthesis of claim 46, wherein the alloy comprises from about 10% by weight to about 40% by weight of the first element.

* * * * *

UNITED STATES PATENT AND TRADEMARK OFFICE
CERTIFICATE OF CORRECTION

PATENT NO. : 7,294,214 B2
APPLICATION NO. : 10/338223
DATED : November 13, 2007
INVENTOR(S) : Charles Horace Craig Page 1 of 1

It is certified that error appears in the above-identified patent and that said Letters Patent is hereby corrected as shown below:

Column 12, line 1, please delete "endonrosthesis" and insert --endoprosthesis-- therefor;

Column 12, line 11, please delete "endonrosthesis" and insert --endoprosthesis-- therefor;

Column 12, line 30, please delete "endonrosthesis" and insert --endoprosthesis-- therefor;

Column 12, line 41, please delete "kcV" and insert --keV-- therefor;

Column 12, line 45, please delete "endonrosthesis" and insert --endoprosthesis-- therefor;

Column 13, line 1, please delete "endonrosthesis" and insert --endoprosthesis-- therefor;

Column 13, line 13, please delete "endonrosthesis" and insert --endoprosthesis-- therefor;

Column 13, line 16, please delete "endoDrosthesis" and insert --endoprosthesis-- therefor;

Column 13, line 53, please delete "endourosthesis" and insert --endoprosthesis-- therefor.

Signed and Sealed this

Nineteenth Day of August, 2008

JON W. DUDAS
*Director of the United States Patent and Trademark Office*